United States Patent [19]

Porteous

[11] Patent Number: 5,016,795

[45] Date of Patent: May 21, 1991

[54] DENTAL PASTE CUP WITH MULTI-FACET INNER BASE

[76] Inventor: Paul D. Porteous, 607 Island View Dr., Port Hueneme, Calif. 93041

[21] Appl. No.: 440,106

[22] Filed: Nov. 22, 1989

Related U.S. Application Data

[63] Continuation-in-part of Ser. No. 353,776, May 18, 1989.

[51] Int. Cl.⁵ .................. B65D 25/10; B65D 1/42
[52] U.S. Cl. ...................... 224/217; 206/63.5; 220/608; 433/49; 366/602
[58] Field of Search ............ 220/66, 70, 72, 83, 220/608, 623, 669, 674, 675; 206/63.5; 224/217; 433/49; 366/602; 269/302.1; 241/29, DIG. 27

[56] References Cited

U.S. PATENT DOCUMENTS

| | | | |
|---|---|---|---|
| 902,109 | 10/1908 | Powell | 224/217 |
| 2,222,741 | 11/1940 | Bush | 224/217 |
| 2,582,245 | 1/1952 | Folli | 220/72 |
| 3,140,796 | 7/1964 | Broida | 220/66 |
| 3,973,693 | 8/1976 | Brocklehurst | 220/70 |
| 4,717,057 | 1/1988 | Porteous | 224/217 |

FOREIGN PATENT DOCUMENTS

| | | | |
|---|---|---|---|
| 105209 | 9/1938 | Australia | 220/83 |
| 175030 | 9/1952 | Austria | 220/66 |
| 1118091 | 11/1961 | Fed. Rep. of Germany | 220/70 |

*Primary Examiner*—George E. Lowrance
*Attorney, Agent, or Firm*—Donald Diamond

[57] ABSTRACT

A dental paste dispensing apparatus includes a molded plastic cup having an open mouth defined by a rim and has an interior for containing dental paste material. A locking mechanism is disposed within the interior for preventing the dental paste material contained therein from rotating with a rotating applicator which is dipped into the paste to obtain an appropriate amount for professional application to the teeth.

7 Claims, 2 Drawing Sheets

DENTAL PASTE CUP WITH MULTI-FACET INNER BASE

CROSS REFERENCE TO RELATED APPLICATION

The present application is a continuation-in-part of design patent application Ser. No. 353,776 filed May 18, 1989

BACKGROUND OF THE INVENTION

1. Field of the Invention

The present invention relates generally to dental dispensing cups and, more specifically, to cups having locking means for preventing rotation of the paste.

2. Description of the Related Art

Dental paste cups are described in U.S. Pat. No. 4,717,057, (Porteous, 1988) and U.S. Pat. No. 4,844,308 (Porteous, 1989), in which a finger mount in integrally molded with the rim of a molded plastic cup, so as to be elastically yieldable to provide a slide-resistant grip when supported on a dental professionals finger. The cup described therein is generally circular with a slightly rounded bottom.

The dental paste which is contained in the dental paste cup is relatively thick and presents a cohesive mass which tends to rotate as a rotating applicator is dipped into the paste. This makes it difficult to obtain an appropriate amount for professional application to teeth. The problem results from the fact that the molded plastic cup is made of a plastic material which has a relatively low frictional coefficient, while the paste has a relatively high viscosity, thereby making the entire contents of the cup rotate with a rotating applicator.

SUMMARY OF THE INVENTION

An object of the present invention is to provide a dental paste cup with paste anti-rotation locking means which prevent the entire contents of the cup from rotating with a rotating applicator.

Another object of the present invention is to provide a dental paste cup which is relatively simple in construction and cost effective to produce.

These and other object of the invention are met by providing a dental paste dispensing apparatus including a molded plastic cup having an open mouth defined by a rim and having an interior for containing dental material, and locking means disposed within the interior for preventing rotation of the dental material when contained therein.

These and other features and advantages of the dental paste cup of the present invention will become more apparent with reference to the following detailed description and drawings.

DETAILED DESCRIPTION OF THE PREFERRED EMBODIMENTS

Figure 1:
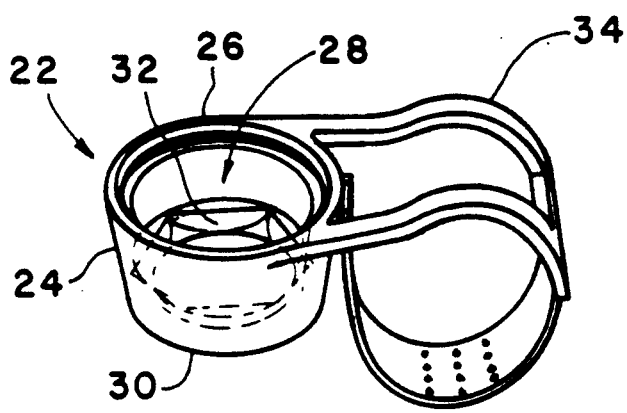
FIG. 1 is a perspective view taken from the top and right side of a dental paste cup according to a first, preferred embodiment of the present invention.

Referring to FIG. 1, a dental dispensing apparatus according to the present invention is generally referred to by the numeral 22. The apparatus includes a molded plastic cup 24 having an open mouth defined by a rim 26. The rim 26 may provide a seat for a plastic cover (not shown) which is snap fitted into the rim 26. The cup 24 has an interior 28 for containing dental paste material (not shown in FIG. 1).

A base 30 of the cup 24 is provided with a geometric configuration on the inside thereof which acts as a locking means in the interior of the cup 24 for preventing rotation of the dental paste when a rotating applicator (not shown) is dipped into the paste to obtain an appropriate amount for professional application to the teeth. When the interior is curvilinear, there is a tendency for the dental paste to rotate as a cohesive mass, thereby rendering it difficult to obtain the proper amount for professional application to the teeth. In a preferred embodiment, the geometric configuration is formed in the interior at the base 30 of the cup. The embodiment of FIGS. 1-3, 5 and 6 shows a hexagonal configuration in which six linear surfaces 32 are disposed around the inner circumference of the cup 24. In the illustrated embodiment, the linear surfaces 32 extend only partially up the curved sidewall of the cup 24. Alternatively., the linear surfaces 32 could extend the full length of the interior of the cup, thereby defining the interior 28 as hexagonally shaped.

Figure 2:
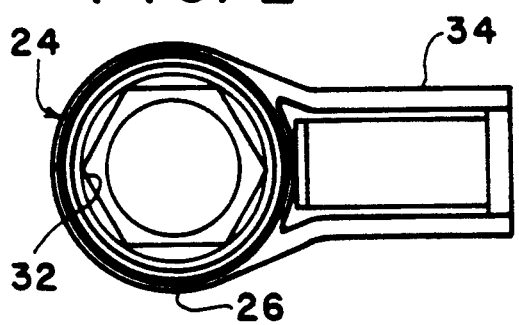
FIG. 2 is a top plan view of the dental paste cup of FIG. 1.
Figure 3:
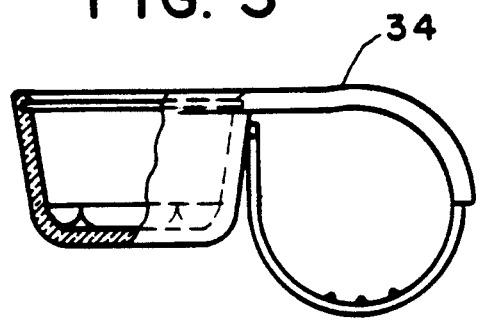
FIG. 3 is a right side elevational view, partly in section, of the embodiment of FIG. 1.

Although the first, preferred embodiment is illustrated in FIGS. 1-3 as having a finger mount 34 integrally formed and extending outwardly from the rim 26, the dental paste dispensing apparatus according to the present invention need not include such structure. Thus, for illustrative purposes the hexagonally shaped interior base portion embodiment is illustrated with the finger mount in FIGS. 1-3, and without the finger mount in FIGS. 5 and 6.

Figure 4:
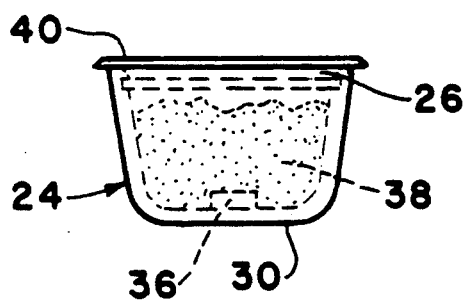
FIG. 4 is a side elevational view of a second, preferred embodiment of the present invention, with dental paste contained in the interior of the cup.
Figure 5:
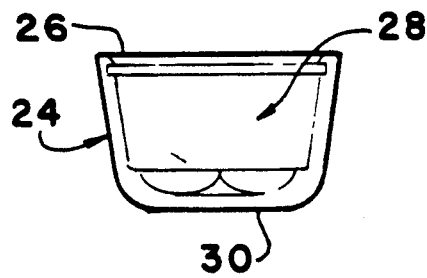
FIG. 5 is a front elevational view of the embodiment of FIG. 1.
Figure 6:
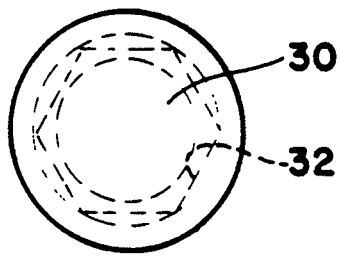
FIG. 6 is a bottom plan view of the embodiment of FIG. 1.

FIG. 4 illustrates an embodiment wherein the locking means is a square-shaped protrusion 36 extending upwardly from an interior of the base 30. The protrusion 36 locks with the dental paste 38 and prevents the paste from rotating in the interior of the cup 24 as a cohesive mass. Prior to dispensing the dental paste 38, a lid 40 is removed from the top of the cup 24 by prying with a finger.

Figure 7:
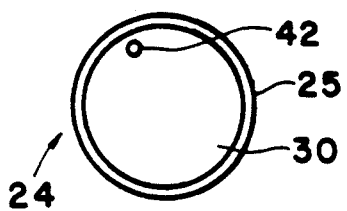
FIGS. 7-18 are top plan views of various embodiments of the dental paste cup of the present invention, showing variations of the locking means disposed in the interior thereof.

Referring to FIG. 7, a schematic representation of an alternative, geometric configuration is illustrated. FIG. 7 is schematic, in that because the preferred embodiments normally have a rounded bottom, the rounded bottom-feature is left out of the illustration to better illustrate the geometric configurations of the locking means. In FIG. 7, the dental paste cup 24 has a sidewall 25 which is circular in shape, thus having a continuous radius. A circular recess 42 is formed in the interior of the base 30, so as to catch a portion of the dental paste which is placed in the interior of the cup. The exact location and depth of the recess 42 is not critical, although it is preferably eccentric to the cup 24.

Figure 8:
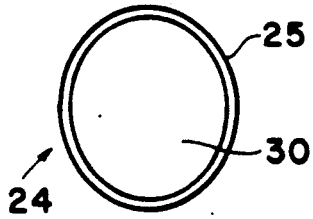

In the embodiment of FIG. 8, the sidewall 25 of the cup 24 is oblated so as to resist the tendency of the dental paste material from rotating with the rotating applicator. Thus, in the embodiment of FIG. 8, the locking means is not a recess or protrusion, but is instead the non-continuous-radius nature of the sidewall 25.

Figure 9:
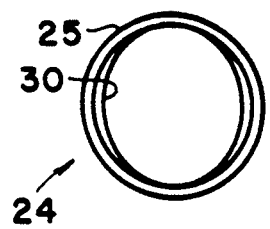

FIG. 9 is a variation of the FIG. 8 embodiment, in which most of the sidewall 25 is circular, but a lower end portion of the sidewall closest to the base 30 becomes oblated, to provide the feature described with reference to FIG. 8.

Figure 10:
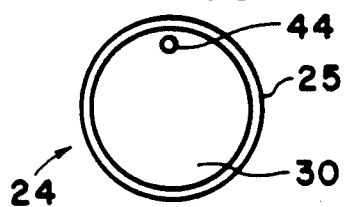

FIG. 10 is a variation of the FIG. 7 embodiment in which the sidewall is circular, and the geometric configuration is a circular protrusion 44 extending upwardly from the base 30. The illustrations appear somewhat identical, since the schematic representations are essentially top plan views. As is the case with the FIG. 7 embodiment, the exact location and height of the protrusion 44 is not critical, although it should be eccentric to the cup 24.

Figure 11:
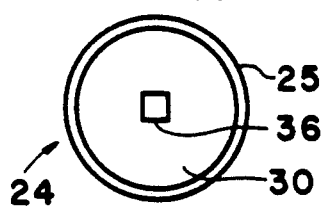

The embodiment of FIG. 11 corresponds to the embodiment illustrated previously in FIG. 4, in which a square-shaped projection 36 extends upwardly from the base 30. As in the previous embodiments, as well as the embodiments to be described, the size and location of the projection is not critical, although with a projection having linear surfaces, such as the square shaped projection 36, it is not undesirable to locate the projection concentrically with the cup 24.

Figure 12:
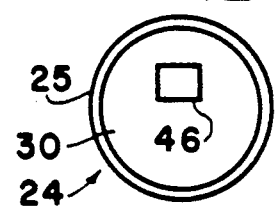

FIG. 12 illustrates a variation of the FIG. 11 embodiment, in which the projection 46 is rectangular in shape and is formed eccentrically to the cup 24.

Figure 13:
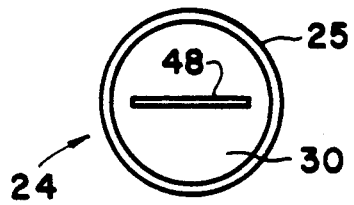

In the embodiment of FIG. 13, a linear projection 48 is formed in the base 30 of the cup 24. Alternatively, the projection 48 may be a recess formed in the base 30. In either case, the dental paste tends to be prevented from rotating by interacting with the geometric formation provided at the base. As a practical matter, the height of the projection 48 is limited to that which would not inhibit dispensing or filling the interior of the cup 24 with the dental paste material. This is true for all of the embodiments described herein.

Figure 14:
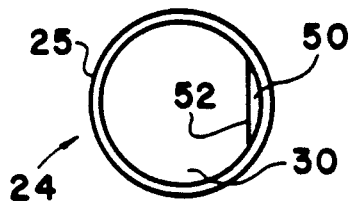

With respect to the embodiment of FIG. 14, the sidewall 25 is circular and the locking means is an arcuate projection 50 having a linear surface 52 which forms a cord with the circular inner diameter of the cup 24. The arcuate projection 52 projects radially inwardly from the circular sidewall 25 and axially upwardly along the circular sidewall. Preferably, the arcuate segment begins at the base 30 and extends upwardly for a length sufficient to prevent rotation of the dental paste. This length may coincide with the complete height of the sidewall 25, or it may simply extend a millimeter or a few millimeters from the base 30.

Figure 15:
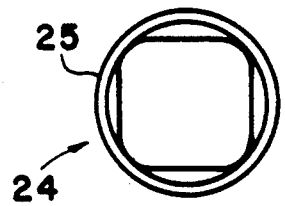

In the embodiment of FIG. 15, the sidewall is circular in shape and the geometric projection is a square having rounded corners tangent to the inner circular diameter of the sidewall 25. In this respect, the embodiment of FIG. 15 is similar to the embodiment described with reference to FIGS. 1-3, 5 and 6, except that the geometric configuration is four-sided.

Figure 16:
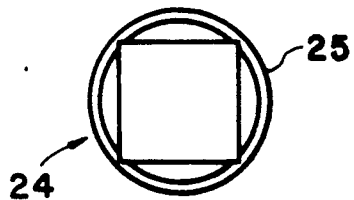

FIG. 16 is a variation of the embodiment of FIG. 15 in which the square geometric configuration has right-angled corners.

Figure 17:
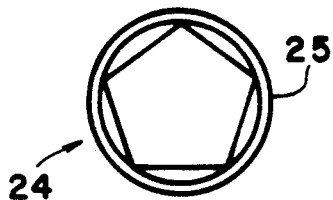

FIG. 17 is another variation of the FIG. 1 embodiment, in which the geometric configuration is five-sided instead of six.

Figure 18:
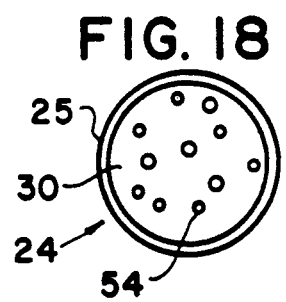

FIG. 18 shows another embodiment in which the sidewall 25 is circular in shape and the locking means is a plurality of random-sized and located circular projections 54 (or recesses).

Figure 21:
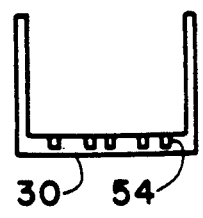
FIG. 21 is a schematic representation of the embodiment of FIG. 18, showing the locking means as depressions in the base of the cup.

FIG. 21 illustrates the FIG. 18 embodiment as recesses 54 formed in the base 30.

Figure 19:
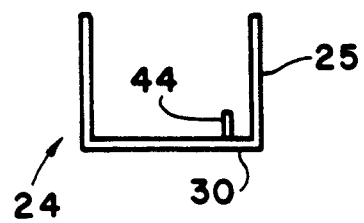
FIG. 19 is a schematic representation of the embodiment of FIG. 10, showing a projection extending upwardly from the base of the cup.
Figure 20:
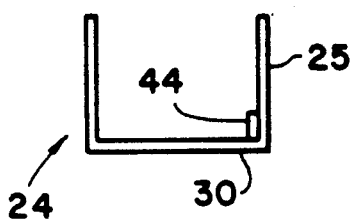
FIG. 20 is a schematic representation of the embodiment of FIG. 14 showing the locking means as a projection extending upwardly from the base of the cup.

FIGS. 19 and 20 show embodiments with circular sidewalls wherein the projections 44 are located at different positions relative to the center of the base 30. The illustrations of FIGS. 19 and 20 demonstrate that the projection 44 may have different sizes, shapes, and/or locations, so long as it is capable of acting as a locking means to prevent rotation of the dental paste.

Numerous modifications and adaptations of the present invention will be apparent to those skilled in the art and thus, it is intended by the followings claims to cover all such modifications and adaptations which fall within the true spirit and scope of the invention.

That which is claimed is:

1. A finger mountable dental paste dispensing apparatus comprising:
   a molded plastic cup having an open mouth defined by a rim and having an interior for containing dental paste material;
   locking means disposed within the interior for preventing rotation of the dental paste material, said locking means comprising an interior sidewall of said cup having a non-continuous radius, and a finger mounted formed on said cup.

2. A dispensing apparatus as claimed in claim 1 wherein said interior sidewall includes at least one linear surface.

3. A dental paste dispensing apparatus according to claim 2 wherein said interior sidewall includes at least four linear surfaces, each forming a cord with the inner circumference of the interior of the cup.

4. A dental paste dispensing apparatus according to claim 1 wherein the interior sidewall of the cup is oblated.

5. A dental paste dispensing apparatus as claimed in claim 1 wherein said finger mount is formed integrally on the rim of the cup.

6. A dental paste dispensing apparatus as claimed in claim 1 further comprising a removable lid snap fitted into the rim of the cup.

7. A dental paste dispensing apparatus as claimed in claim 1 wherein the molded plastic cup has a low frictional coefficient, and the dental paste to be contained therein has a high viscosity and tendency to agglomerate.

* * * * *